(12) United States Patent
Brasile

(10) Patent No.: US 8,748,164 B2
(45) Date of Patent: Jun. 10, 2014

(54) DELIVERY SYSTEM FOR CELL-BASED THERAPIES

(75) Inventor: Lauren Brasile, Albany, NY (US)

(73) Assignee: Breonics, Inc, Albany, NY (US)

( * ) Notice: Subject to any disclaimer, the term of this patent is extended or adjusted under 35 U.S.C. 154(b) by 0 days.

(21) Appl. No.: 13/346,650

(22) Filed: Jan. 9, 2012

(65) Prior Publication Data

US 2012/0179139 A1    Jul. 12, 2012

Related U.S. Application Data

(60) Provisional application No. 61/430,633, filed on Jan. 7, 2011.

(51) Int. Cl.
*A01N 1/00* (2006.01)
*A61M 31/00* (2006.01)

(52) U.S. Cl.
USPC ..................................... 435/284.1; 604/522

(58) Field of Classification Search
USPC ................................ 604/522, 506; 435/284.1
See application file for complete search history.

(56) References Cited

U.S. PATENT DOCUMENTS 6,642,045 B1 * 11/2003 Brasile ....................... 435/284.1
2002/0193335 A1 * 12/2002 Hesson et al. ................. 514/44

* cited by examiner

*Primary Examiner* — Nicholas Lucchesi
*Assistant Examiner* — Leah Stohr
(74) *Attorney, Agent, or Firm* — Heslin Rothenberg Farley & Mesiti P.C.; Kathy Smith Dias

(57) ABSTRACT

A warm perfusion system that has the ability to support a tissue or organ at a near normal metabolic rate provides the mechanism not only for restored oxidative metabolism of the organ but for the delivery of cells, cell-based therapeutics, and growth and differentiation factors to a damaged tissue or organ. Subsequent to delivery of therapeutic cells, such as stem cells or progenitor cells, to the damaged organ, the cells can be prompted to grow, multiply and differentiate, thereby restoring damaged tissue.

9 Claims, 2 Drawing Sheets

DELIVERY SYSTEM FOR CELL-BASED THERAPIES

CROSS-REFERENCE TO RELATED APPLICATIONS

This application claims the priority of U.S. provisional application 61/430,633 filed Jan. 7, 2011, the entire disclosure of which is incorporated herein by reference.

FIELD OF THE INVENTION

The present disclosure relates generally to the use of a metabolic support system for the biologic delivery of therapeutic agents. In particular, the disclosure pertains to the delivery of cell-based therapies useful for the repair of damaged tissues and organs.

BACKGROUND OF THE INVENTION

Reports regarding the ability to deliver mesenchymal stem cells (MSC) in vivo intravascularly to ischemically damaged kidneys can be found in the literature. Preclinical and clinical studies have demonstrated that adult stem cells may be recruited from the circulation to actively participate in the regeneration of cardiac and renal tissue. It is well documented that cells in the bloodstream, including immune cells, inflammatory cells and tumor cells, move in and out of tissues and organs. Furthermore, studies also demonstrate that in vivo intravascular delivery of MSC and progenitor cells "home" to the site of tubular damage. Using intravital videomicroscopy it has been shown that by three hours of injecting cells into the circulation, homing occurs by migration of the injected cells from the circulation into targeted organs. However, it is currently not possible to quantify the number of seeded cells that are retained in the targeted tissues. Likewise with in vivo seeding it is not currently feasible to determine or control untargeted sites where the infused cells may locate. Therefore, currently there is no way to control the delivery of a cell-based therapy that is administered in vivo.

Another problem associated with in vivo infusion of stem, MSC or progenitor cells is that very few blood vessels are found near the engrafted cells; this is consistent with injection into areas of ischemic damage where normal blood, flow has been interrupted. Poor blood supply has been reported to limit the growth of implanted cells and to also decrease the lifespan if in fact differentiation does occur. (16)

Therefore, the in vivo delivery of stem cells by intravascular infusion is not controllable. The uniqueness of this present invention is the use of a closed-loop ex vivo perfusion system rather than an in vivo infusion. By using a closed-loop perfusion system with an acellular, near-normothermic solution the result is a controlled delivery where the cells can be tracked with the number remaining in the vascular compartment and in perfusion circuit can be quantified. It also provides the opportunity to eliminate the significant side-effects that occur with systemic administration of MSC or progenitor cell therapy. These side-effects include nausea, vomiting, diarrhea, loss of appetite, hair loss, mouth sore, ulcers, skin rashes, fatigue, reduction in red blood cells and white blood cells counts leading to susceptibility for infection and bleeding. These side-effects can persist for days post-treatment. This makes the invention an enhanced approach for not only greatly expanding the donor pool of organs for transplantation, but also for tissue-engineering and regenerative medicine as a whole.

SUMMARY OF THE INVENTION

The present disclosure provides delivery of cells and cell-based therapeutics via a closed-loop ex vivo perfusion system which provides numerous advantages over an in vivo infusion system. A closed circuit perfusion system with an acellular perfusion solution enables a controlled delivery of cell-based therapies where the status/viability of injected cells can be tracked and the number of cells in the vascular compartment and in the perfusion circuit can be monitored and quantified. It also provides the opportunity to eliminate the significant side-effects that occur with systemic administration of MSC or progenitor cell therapy. These side-effects include nausea, vomiting, diarrhea, loss of appetite, hair loss, mouth sore, ulcers, skin rashes, fatigue, reduction in red blood cells and white blood cells counts leading to susceptibility for infection and bleeding. These side-effects can persist for days post-treatment. This makes the invention an enhanced approach for not only greatly expanding the donor pool of organs for transplantation, but also for tissue-engineering and regenerative medicine as a whole.

In one aspect, therefore, the disclosure relates to a method for the delivery of cells to a target tissue or organ, the method comprising isolating said target tissue or organ from the circulatory system of a body; flushing the tissue or organ with a non-blood buffered physiological solution to remove blood and blood products; maintaining the target tissue or organ with a recirculating non-blood perfusion solution at 25° C.-37° C., to maintain the tissue or organ in a near normal metabolic state and contacting the tissue or organ during the perfusion period with the cells or cell-based therapeutic agent by adding the cells/agent to the recirculating non-blood perfusion solution.

In a related aspect, the present disclosure relates to a method for the delivery of a cell-based therapeutic agent to an organ or tissue, the cell-based repair of which is desired. The method comprises flushing an organ or tissue in which the treatment is desired with a buffered physiological solution to remove blood and blood products; establishing the organ or tissue in a perfusion system comprising a warm non-blood perfusion solution, where the perfusion system is capable of restoring oxidative metabolism in the organ or tissue and maintaining the organ or tissue in a near-normal metabolic state at 25°-37° C.; and contacting the organ or tissue with a cell-based therapeutic agent by introducing it via the recirculating perfusion solution.

BRIEF DESCRIPTION OF THE DRAWINGS

FIG. 2a shows a section of renal tubule epithelium of a kidney to which human tubule epithelial precursor cells have been delivered; FIG. 2b is a fluorescent micrograph of the same section showing that the cells, which were fluorescently labeled prior to delivery, are limited to the tubule epithelium.

DETAILED DESCRIPTION OF THE INVENTION

Figure 1:
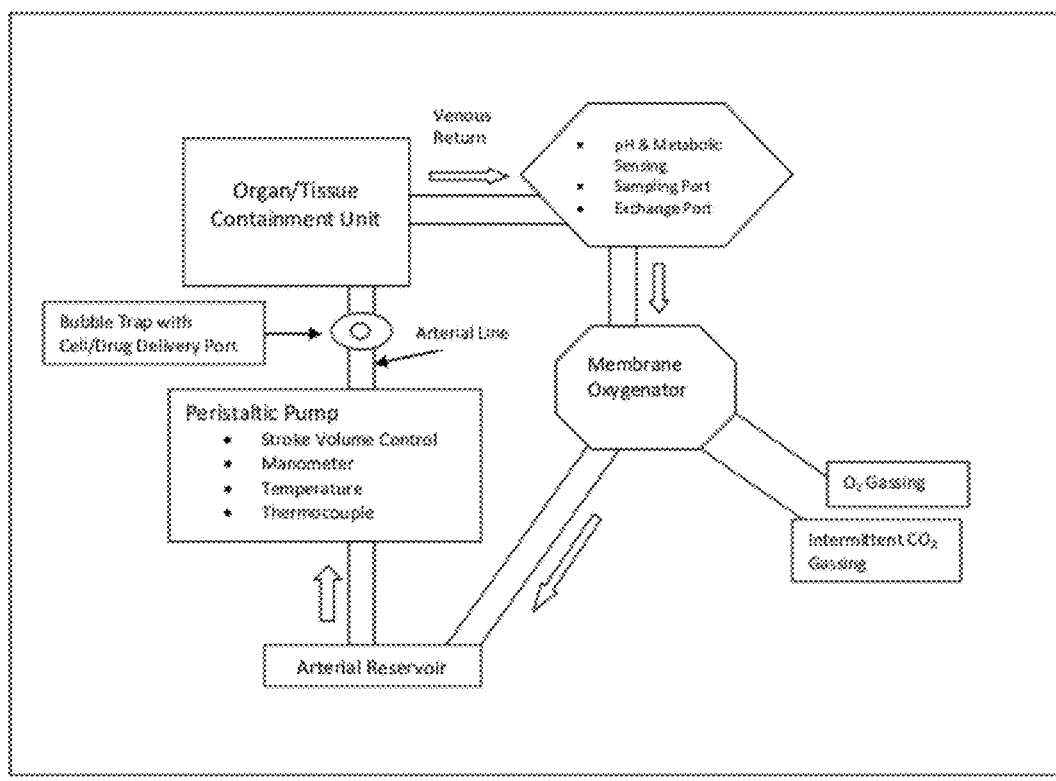
FIG. 1 is a schematic showing the basic components of a warm perfusion system suitable for practicing the cell delivery method disclosed herein.

All references, published applications, and patents cited herein, including U.S. Pat. Nos. 6,024,698, 5,843,024, 5,699, 793, 5,599,659 and 5,643, 712 are hereby incorporated by reference in their entirety into the subject application.

In the description that follows, certain conventions will be followed as regards the usage of terminology.

The term "organ" or "tissue", as those terms are known to those in the art refers a collection of tissues or cells, respectively characterized by their ability to perform a particular physiologic function. In one aspect, the method of the present invention is useful to repair a potentially damaged but viable section of the body, for example, an intact organ including, but not limited to, a kidney, heart, liver, lung, small bowel, pancreas, brain, eye, skin, limb or anatomic quadrant.

The term "closed-loop" with respect to the perfusion pathway, refers to a continuous perfusion pathway in which the perfusion solution is constantly recirculated. A "closed-loop" in not intended to preclude the addition of perfusion constituents including the replenishment of cell nutrients as they are exhausted due to active metabolism by the tissue or organ.

The terms "perfusion solution" and "perfusate" are used interchangably and refer to a non-blood buffered physiologic solution that provides means for reestablishing cellular integrity and function in organs which may have experienced ischemic damage prior to or during isolation and further, enables an organ or tissue to be maintained at a near normal rate of metabolism. The term "non-blood" is intended to exclude perfusates comprising substantially whole blood or its individual components. The perfusion solution of the present invention may, however, contain a minimal amount of whole blood or a blood component, for example, red blood cells, serum or plasma.

"Isolating" an organ or tissue from a body means that the organ or tissue is separated or removed from the circulatory system of the body, either to allow "in situ" or "ex vivo" treatment of the organ or tissue. Minimally, isolation requires removing or interrupting the arterial source of blood feeding the desired tissue or organ as well as interruption of venous outflow. Where the tissue or organ is completely excised from the body for ex vivo treatment, then the enervation and lymphatics of the tissue or organ are also isolated.

The terms "near normal rate of metabolism" and "near normal metabolic rate" are defined as about 70-100% of the normal rate of metabolism for a particular organ as determined by measuring and evaluating whether functional characteristics of an organ, such as those described in U.S. Pat. No. 5,699,793, are within the range associated with normal function for that particular organ. Examples of functional characteristics include, but are not limited to, electrical activity in a heart as measured by electrocardiogram; physical and chemical parameters of organ product, for example, oxygen consumption and glucose utilization which can be ascertained from the change in the concentrations of oxygen and glucose in the perfusate during the perfusion period; pancreatic enzymes; heart enzymes; creatinine clearance and filtration functions of the kidneys, specific gravity of urine and the like.

The term "cell-based therapeutic agent" refers to any cells or mixture of cells which provide a therapeutic effect. The cell-based therapeutic agent may be included in a composition that further includes growth or differentiations factors to effect or facilitate a functional, metabolic, immunogenic or genomic change in an organ or tissue. Cells for use in an embodiment of the method of treatment include but are not limited to embryonic stem cells, adult stem cells, mesenchymal stem cells, pancreatic islet cells, hematopoietic progenitor cells.

The term "stem cells", as that term is known in the art, refers to cells that have the capability of self-renewal and the capability to give rise to at least one and often a number of specialized cell types.

The terms "progenitor cell" and "stem cell" are sometimes equated. Progenitor cells isolated from complex differentiated tissues and organs have also demonstrated significant potential to differentiate in to functional cells to replace diseased or lost differentiated cells. A progenitor cell, like mesenchymal and hematopoietic stem cells, has a tendency to differentiate into a specific type of cell. However, its differentiation potential is more limited and specific than a stem cell and is pushed to differentiate into its "target" cell. The most important difference between stem cells and progenitor cells is that stem cells can replicate indefinitely, whereas progenitor cells can divide only a limited number of times. Mesenchymal stem cells isolated from both bone marrow and peripheral blood as well as progenitor cells isolated from differentiated tissues have been shown to accelerate healing processes.

The term "mesenchymal stem cells (MSC)" refers to multipotent stem cells that can differentiate into a variety of cell types, for example, osteoblasts, chondrocytes, myocytes, adipocytes, and beta-pancreatic islet cells.

Although not immortal, MSCs have the ability to be expanded in culture while retaining their growth and differentiation potential. MSCs are identified by the expression of molecular markers that include CD 105 (SH2) and CD73 (SH3/4) and are negative for hematopoietic markers CD34, CD45, and CD 14.

There are several technologies that use ex vivo perfusion to tissue engineer organs. To date, however, these technologies have used de-cellularized organs and artificial scaffolding materials to demonstrate the ability to re-seed denuded hearts and livers, for example. The de-cellularized organs provide the scaffolding for the bioengineered construct. These bioengineering efforts have focused on re-seeding with one or two cell types and do not represent the various heterogenous cell types required to provide normal organ function.

The present method provides a unique mechanism for the introduction of exogenous cells into a tissue or organ and therefore, for potentially re-seeding damaged organs with the several millions of cells required for replacing the denuded sites of injury. The method of the disclosure also restores characteristics of the normal vasculature resulting in its regeneration, restoration of its normal barrier function and surface polarity. The ability to re-seed damaged areas within organs and tissues while simultaneously restoring normal vascular wall integrity leads to the regeneration of the organ resulting in life-sustaining function.

Cell Isolation and Preparation

While it has not been definitively demonstrated that stem cells possess the plasticity across diverse lineages, there is substantial evidence that hematopoietic stem cells isolated from blood and mesenchymal cells isolated from bone marrow can play an important role in healing. Compared to embryonic stem cells, adult stem cells, despite having a more restricted differentiation potential, can be isolated from blood, spleen, liver and bone marrow. Both hematopoietic stem cells and mesenchymal cells are capable of self-renewal and can differentiate into a variety of cell types. Characteristics of MSCs which make them particularly appealing for cell-mediated therapy is their low immunogenicity and tissue-homing ability.

Bone marrow is the most common source of MSCs; mesenchymal and hematopoietic stems cells are typically isolated from the mononuclear layer of marrow or blood after separation using density gradient centrifugation. MSCs have, however, been isolated from various other sources, including placenta, amniotic fluid, cord blood and adipose tissue. Isolated cells express markers that are not restricted in their expression to stem cells.

MSCs can also be functionally isolated from primary tissue based on their capacity to adhere to a plastic substrate. Another suitable method for MSC isolation is based on antibody-mediated specificity.

In one embodiment, MSCs are obtained by bone marrow aspirate in accordance with well established techniques. Subsequently, the isolated cells are suspended at about $10^6$ cells per ml in basal tissue culture media such as Dulbecco's modified Eagle's medium supplemented with fetal bovine serum (about 2-10%). The isolated cells are maintained in tissue culture using culture protocols known to those of skill in the art.

In one embodiment, the method involves isolating an organ, tissue or specific area of anatomy, generally, one in which injury has occurred, from the rest of the physiologic system by removing or interrupting the arterial source of blood feeding the desired organ or tissue(s). Likewise, the venous outflow from the organ or section of anatomy is interrupted and the venous effluent is collected. If the tissue is completely excised from the body, then the enervation and lymphatics of the tissue(s) are also isolated.

Next, the organ or tissue is flushed through the arterial system with a cell-free, buffered physiological solution at a temperature of about 25°-37° C. to remove blood and blood products from the organ or tissue. The organ is then placed in a exsanguinous metabolic support system (hereinafter referred to as "EMS") such as that described in U.S. Pat. No. 6,642,045, the contents of which are incorporated herein by reference, that is capable of maintaining the organ at a near-normal metabolic rate. The organ is perfused with a warm perfusion solution, for example, the solution described below, while various parameters of the perfusion are monitored by the system and regulated as necessary to maintain adequate metabolism of the organ or tissue.

The organ's physiological processes are maintained and controlled by the EMS system. The EMS perfusion system delivers a warm perfusion solution containing all the constituents necessary to reestablish, where necessary, and support oxidative metabolism by the organ. The perfusion system may also reprocess the perfusion solution to ensure a continuous supply of nutrients and chemical energy substrates and remove metabolic by-products. Additionally, the EMS monitors and controls various parameters of the perfusion including temperature, vascular pressures, perfusion flow rate, OsM, pH, $PaO_2$, $PaCO_2$, nutrient delivery and the removal of waste products.

Perfusion Solution

Perfusion of the isolated organ or section of anatomy with a solution at near physiologic temperature of about 25° C. to 37° C., in accordance with the disclosed method, performs a number of functions. It maintains the cellular environment at physiologic pH and maintains near normal oxygenation, temperature, and osmolarity. It maintains the normal barrier function of the tissue to macromolecules, thereby resulting in stable perfusion pressures and stable vasculature flow rates. It adequately dilates and fills the vasculature, delivers adequate trophic factors to maintain a near normal level of metabolism in the isolated organ or section of anatomy and supports the artificially interrupted aerobic metabolism by providing high energy compounds. It supports ongoing oxidative metabolism with supplemental substrates that may include, but are not limited to, glucose, pyruvate, and uridine 5-triphosphate (UTP). The ongoing oxidative metabolism is further supported by maintaining the adenine compound pool. The citric acid cycle and the electron transport chain are supported by providing adequate substrate delivery to continue metabolic support and function in the isolated organ and tissues. The ongoing metabolism supported by the method and solution of the invention provides adequate metabolites and nutrients to maintain the tissue integrity with tight cellular functions and normal membrane polarity.

Organ preservation systems and perfusate solutions useful in practicing the present method are known in the art as comprising a base solution that consists of a buffered physiological solution, such as a salt solution or a cell culture-like basal medium, to which is added a variety of defined supplements. The warm perfusion solution used in the present method employs such a base solution containing amino acids in quantities sufficient to support protein synthesis by the metabolizing organ, ions, physiologic salts, serum proteins, carbohydrates, and a buffering system for maintaining pH at physiologic levels. Furthermore, the perfusion solution of the present invention has been designed to support the nutritional and metabolic needs of the vascular endothelium within a graft, thereby maintaining the integrity of the vasculature and, subsequently, the normal permeability of the organ.

The buffered basal medium may be any commercially available salt solution or cell culture medium, (e.g., Hank's BSS, Earle's BSS, Ham's F12, DMEN, Iscove's MEM, M199, RPMI 1640, RSM-210.) In one embodiment of the perfusion solution of the present invention, a bicarbonate buffer system is employed. The bicarbonate buffer works in concert with the respiratory gas controller subsystem of the EMS system to automatically maintain the pH of the perfusion solution in a narrow range, 7.0 to 7.6, and more preferably, 7.30-7.45, which approximates respiratory control of blood pH by the lungs.

To the basal medium are added a number of supplements, including, but not limited to, essential and non-essential amino acids, growth factors, vasodilators, vitamins, and chemical energy substrates, in a physiologically effective amount to support oxidative metabolism by the organ or tissue.

Amino acids to be included in the perfusion solution of the present invention include the basic set of 20 amino acids and may be D- or L-amino acids, or a combination thereof, or may be modified amino acids, such as citrulline, ornithine, homocysteine, homoserine, β-alanine, amino-caproic acid and the like, or a combination thereof.

Chemical energy substrates added to the perfusion solution may include pyruvate, glucose, ATP, AMP, coenzyme A, flavin adenine dinucleotide (FAD), thiamine pyrophosphate chloride (cocarboxylase), β-nicotinamide adenine dinucleotide (DPN), β-nicotinamide adenine dinucleotide phosphate (TPN), uridine 5'triphosphate (UTP) chloride. The chemical energy substrates comprise from about 0.01% to about 90% by volume of the combination of supplements added to the base solution in preparing the perfusion solution of the present invention.

Also added to the basal medium are nucleic acids for DNA repair and synthesis including 2' deoxyadenosine, 2' deoxyguanosine, 2' deoxycytidine, adenosine, thymidine, guanosine, cytidine and uridine. The solution of the present invention may further comprise hormones, such as insulin, and thyroid stimulating hormone (TSH) and growth factors (GF), such as platelet-derived growth factor (PDGF), fibroblast growth factor (FGF-1, FGF-2), insulin-like GF I and II, epithelial GF, epidermal GF, brain-derived FGF, somatomedins A1, A2, B and C, nerve growth factor (NGF), vascular endothelial growth factor (VEGF), heparin-binding growth factor (HBGF), endothelial cell growth factor (ECGF), transforming growth factor (TGF), glucocorticoids and urogastone. Also included are cytokines such as IL-1, colony stimulating factor (CSF), and erythropoietin.

The perfusion solution also comprises serum albumin and/or mucopolysaccharides such as chondroitin sulfate B, heparin, petastarch, hetastarch, and plasma expanders as a source of colloid, and lipids, such as linoleic acid, arachidonic acid, linolenic acid, eicosapentaenoic acid, docosahexaenoic acid, oils. Additionally, attachment factors, antioxidants, vasodilators and impermeants may be included in the perfusion solution of the present invention.

In one embodiment, the high osmolar solution may be used for the initial organ flushing, and as a perfusate for long term maintenance of an organ in the EMS system using warm preservation technology (18°-35° C.) without extreme hypothermia. The solution has been designed to support the nutritional and metabolic needs of the vascular endothelium within a graft, thereby maintaining the integrity of the vasculature and subsequently the normal permeability of the organ. While some of the components of the solution of the present invention are similar to those of other known tissue culture media, and of other known preservation solutions for organ transplantation with extreme hypothermia, the solution was specifically designed to potentiate the simultaneous growth of microvessel and large vessel endothelial cells, to support the integrity of vascular endothelium within a graft; and to support normal permeability and metabolism without extreme hypothermia. The enhanced ability of the solution to serve as a preservation solution for organs for transplantation using a warm preservation technology, may be attributed to supplementation with serum albumin as a source of protein and colloid, vasodilators to ensure adequate dilation of the vasculature, trace elements to potentiate viability and cellular function, pyruvate and adenosine for oxidative phosphorylation support; transferrin as an attachment factor; insulin and sugars for metabolic support; and glutathione to scavenge toxic free radicals as well as a source of impermeant; cyclodextrin as a source of impermeant, scavenger and potentiator of cell attachment and growth factors; a high Mg concentration for microvessel metabolism support; mucopolysaccharides, comprising primarily chondroitin sulfates and heparin sulfates, for growth factor potentiation and hemostasis; and ENDO GRO™ as a source of colloid, impermeant and growth promoter. As a result, the preservation solution of the present invention has been found to preserve organs without extreme hypothermia, and does not present the common problems encountered with cold perfusates, namely, edema, vasospasm, depletion of ATP stores, shutdown of ion pumps, glycolysis, and the generation of cold-induced toxic free radical intermediates. The preservation solution of the present invention provides for more efficacious preservation thereby presenting the potential to utilize an expanded donor pool, namely, the non-heart beating cadaver donors.

It will be appreciated by those skilled in the art that other components may be substituted for a functionally equivalent compound to achieve the same result. For purposes of illustration, and not limitation, Table 1 lists components of one embodiment of the perfusion solution used in practicing the method of the present invention.

TABLE 1

| | |
|---|---|
| DL-Alanine | 0.12 g/L |
| L-Arginine HCl | 0.14 g/L |
| DL-Aspartic Acid | 0.12 g/L |
| L-Cysteine HCL•$H_2O$ | 0.022 g/L |
| L-Cystine 2HCl | 0.052 g/L |

TABLE 1-continued

| | |
|---|---|
| DL-Glutamic Acid | 0.2672 g/L |
| L-Glutamine | 0.2 g/L |
| Glycine | 0.1 g/L |
| L-Histidine HCl•$H_2O$ | 0.04376 g/L |
| L-Hydroxyproline | 0.02 g/L |
| DL-Isoleucine | 0.08 g/L |
| DL-Leucine | 0.24 g/L |
| L-Lysine HCl | 0.14 g/L |
| DL-Methionine | 0.06 g/L |
| DL-Phenylalanine | 0.10 g/L |
| L-Proline | 0.08 g/L |
| DL-Serine | 0.10 g/L |
| DL-Threonine | 0.12 g/L |
| DL-Tryptophan | 0.04 g/L |
| L-Tyrosine•2Na | 0.11532 g/L |
| DL-Valine | 0.10 g/L |
| Adenine Hemisulfate | 0.02 g/L |
| Adenosine Triphosphate•2Na | 0.002 g/L |
| Adenylic Acid | 0.0004 g/L |
| Alpha Tocophercol Phosphate•2Na | 0.00002 g/L |
| Ascorbic Acid | 0.0001 g/L |
| D-Biotin | 0.00002 g/L |
| Calciferol | 0.0002 g/L |
| Cholesterol | 0.0024 g/L |
| Choline Chloride | 0.001 g/L |
| Deoxyribose | 0.001 g/L |
| Folic Acid | 0.00002 g/L |
| Glutathione (Reduced) | 0.0001 g/L |
| Guanine HCl | 0.0006 g/L |
| Hypoxanthine | 0.0006 g/L |
| Menadione (Na bisulfite) | 0.00003 g/L |
| Myo-Inositol | 0.00011 g/L |
| Niacinamide | 0.00005 g/L |
| Nicotinic Acid | 0.00005 g/L |
| PABA | 0.0001 g/L |
| D-Pantothenic Acid Ca | 0.00002 g/L |
| Polyoxyethylenesorbitan Monoleate | 0.04 g/L |
| Pyridoxal HCl | 0.00005 g/L |
| Pyridoxine HCl | 0.00005 g/L |
| Retinol Acetate | 0.00028 g/L |
| Riboflavin | 0.00002 g/L |
| Ribose | 0.001 g/L |
| Thiamine HCl | 0.00002 g/L |
| Thymine | 0.0006 g/L |
| Uracil | 0.0006 g/L |
| Xanthine Na | 0.00069 g/L |
| Calcium Chloride•$2H_2O$ | 0.265 g/L |
| Ferric Nitrate•$9H_2O$ | 0.00144 g/L |
| Magnesium sulfate (anhydrous) | 1.20 g/L |
| Potassium chloride | 0.4 g/L |
| Sodium Acetate (anhydrous) | 0.1 g/L |
| Sodium Chloride | 6.8 g/L |
| Sodium Phosphate Monobasic (anhydrous) | 0.244 g/L |
| Glucose | 2.0 g/L |
| Insulin | 0.01 g/L |
| Serum albumin | 30.0 g/L |
| $NaHCO_3$ | 4.4 g/L |
| Pyruvate | 0.22 g/L |
| Transferrin | 0.1 g/L |
| Serum | 100 ml |
| Impermeant (cyclodextrin) | 0.5 g/L |
| Mucopolysaccharide (chondroitin sulfate B) | 0.004 g/L |
| ENDO GRO ™ (growth factor) | 0.20 g/L |
| heparin | 0.18 g/L |
| chemically modified hemaglobin* or perfluorochemical emulsion* | 216 mg/L 20% (v/v) |
| Coenzyme A | 0.010 g/L |
| FAD | 0.004 g/L |
| DPN | 0.028 g/L |
| Cocarboxylase | 0.004 g/L |
| TPN | 0.004 g/L |
| 2'deoxyadenosine | 0.042 g/L |
| 2'deoxyguanosine | 0.042 g/L |
| 2'deoxycytidine | 0.042 g/L |
| thymidine | 0.042 g/L |
| adenosine | 0.042 g/L |
| guanosine | 0.042 g/L |
| cytidine | 0.042 g/L |

TABLE 1-continued

| | |
|---|---|
| uridine | 0.042 g/L |
| ATP | 0.002 g/L |
| AMP | 0.002 g/L |
| UTP | 0.004 g/L |

*as an oxygen carrier

In one embodiment, the perfusion solution used contains one or more oxygen transporting compounds ("oxygen carrying agents") that function to provide molecular oxygen for oxidative metabolism to the organ. Such oxygen carrying agents are well known to those skilled in the art and include, but are not limited to, hemoglobin, stabilized hemoglobin derivatives (made from hemolyzed human erythrocytes such as pyridoxylated hemoglobin), polyoxethylene conjugates (PHP), recombinant hemoglobin products, perfluorochemical (PFC) emulsions and/or perfluorochemical microbubbles (collectively referred to as "perfluorochemical"). One such oxygen carrier is a perfluorochemical such as perflubron emulsion (perfluoroocytl bromide, PFOB). Other perfluorochemical emulsions said to be useful as oxygen carrying agents are described, for example, in U.S. Pat. Nos. 5,403,575; 4,868,318; 4,866,096; 4,865,836; 4,686,024; 4,534,978; 4,443,480; 4,423,077; 4,252,827; 4,187,252; 4,186,253; 4,110,474; and 3,962,439. Such liquid PFC emulsions include, but are not limited to perfluorooctyl bromide, perfluorooctyl dibromide, bromofluorocarbons, perfluoroethers, Fluosol DA™, F-44E, 1,2-bisperfluorobutyl-ethylene, F-4-methyl octahydroquinol-idizine, 9 to 12 carbon perfluoro amines, perfluorodecalin, perfluoroindane, perfluorotrimethyl bicycle [3,3,1] inane, perfluoromethyl adamante, perfluorodimethyl adamantine. Such oxygen carrying agents comprise from about 0% to about 59% by volume of the supplements which are added to, and dissolved in, the base solution in preparing the perfusion solution of the present invention; or about 0% to about 20% of the total perfusion solution (v/v).

Alternatively, red blood cells (RBC) may be used as an oxygen carrier in an effective amount to support metabolism by the organ being perfused (about 0.1% to 5%.) Generally, about 5 cc of RBC per 500 ml of perfusion solution (that is, about 1%) is an effective amount. When compared to perfluorochemical emulsion or conjugated hemoglobin, RBC provides oxygen concentrations equivalent to the oxygen consumption by the metabolizing organ. This generally occurs at the rate of 0.1-0.3 cc/min/gm. Additionally, after 24 to 48 hours of perfusion, there was no evidence that the RBC were cretinated. Therefore, an amount of RBC in this range does not present the problem of mechanical damage to the organ associated with blood-based perfusates.

Organ Perfusion and Monitoring

A warm perfusion system that employs a closed-loop perfusion pathway provides enhanced targeting of cells to sites of tissue damage. In one embodiment, the delivery system is comprised of an optimized solution containing growth and trophic factors and a perfusion control system that maintains the redox potential of the substrates that are maintained in a non-equilibrium state.

While the exact molecular basis for homing of seeded cells has not been fully delineated, several mechanisms have been suggested, including specific ligands and their receptors, such as those for cytokines, CD44, αB1 integrins, etc. CD44 is a type 1 transmembrane glycoprotein that is known to play a role in wound healing. In the kidney CD44 is up-regulated on injured tubule epithelial and capillary cells. The exposure of extracellular matrices due to damage to the tubular epithelium following ischemia provides for receptor specific binding of MSC and renal progenitor cells. During the period of perfusion the application of extracellular matrix proteins are deposited on the denuded areas the result in enhanced ligand-specific binding of the seeded precursor cells.

The addition of differentiation factors into the circulating perfusate provides the signal transduction for the seeded precursor cells to develop into fully differentiated cells that can replace the damaged cells. The ability to support the differentiation of precursor cells that home to the sites of damage within the perfusing organ results in the regeneration of the damaged part of an organ leading to the restoration of normal function.

The delivery of growth factors into the circulating perfusate during the period of perfusion provides the signal transduction that results in the proliferation of the seeded cells. The replication of the seeded cells within the organ and in the sites of damage where the cells home results in the ability to fully regenerate the damaged components in an organ while it is isolated from its normal vascular flow and the rest of the physiologic system.

For example, the shortage of transplantable kidneys represents a major limiting factor to the number of procedures that can be performed. This invention represents a potential near-term solution by radically expanding kidney donor criteria. The tissue regenerating technology can be used ex vivo to treat and repair kidneys and ex-renal organs for transplantation. The technology can be used to replace the renal tubule epithelium following severe damage caused by acute injury such as ischemia, trauma or secondary to sepsis, etc. The technology can also repair renal and extra-renal damage as a result of chronic injury such as autoimmune disease, chronic allograft rejection, etc.

By seeding ischemically damaged kidneys with bone marrow derived stem and mesenchymal cells or progenitor cells to repair the damaged tubule epithelium a period of acute tubular necrosis (ATN) post-transplantation can be prevented. The invention is a biologic delivery system to recover and repair severely damaged tissues and organs. In addition to providing more allografts, the significance of ameliorating ATN is the possibility of also eliminating inflammatory and immunologic responses associated with chronic rejection.

What makes the biologic delivery technology of this invention unique is the ability to resuscitate and repair damaged organs ex vivo by re-seeding damaged areas after the damage has already occurred; rather than being a protective prophylactic. This unique ability is transformational because it changes today's limitation of recovering kidneys from within minutes of death to the possibility of recovering cadaveric donor organs from within a window of several hours post-mortem. Currently the ability to "repair" organs during ex vivo perfusion is limited to restoring cytoskeletal integrity that entails new synthesis rather than actual cell replacement. Therefore, the ability to replace the loss tubular epithelium in uncontrolled decease by cardiac death, referred to as the DCD kidney donor, holds the potential to reduce the severity and duration of acute tubular necrosis (ATN). The invention provides a cell-based therapy for the deposition, differentiation and integration of the seeded stem, mesenchymal and progenitor cells that leads regeneration while a tissue or organ is separated from its systemic vascular flow.

The cell delivery method disclosed herein has the following advantages over current cell-seeding methods:
 1. The ability to deliver human bone marrow derived stem cells, mesenchymal and progenitor cells to the organ parenchyma during ex vivo perfusion.

2. The ability to home the seeded cells to the sites of damage.
3. The ability for the seeded cells to fully replenish the areas of damage leading to the regeneration of the organ.
4. The continued metabolism ex vivo provides the ability to perform effective prognostic testing to prospectively evaluate organ viability, quantification of the cell-based therapy and function prospectively.

EXAMPLES

Example 1

Establishing the Organ in the Delivery System

The organ or tissue to be treated is established in a sterile organ chamber of a warm perfusion system as described in U.S. Pat. No. 6,642,045 (incorporated herein by reference.) A cannula is placed in the major arterial vessel within the organ or tissue through which the warm, oxygenated, pH regulated nutrient solution is delivered via a pulsatile perfusion pump. The pH, temperature, pressures, nutrient composition, partial pressure of oxygen and carbon dioxide of the perfusate are tightly controlled during perfusion within a pre-determined range to support optimal metabolic rate.

Sampling ports provide for close monitoring of metabolism and synthetic functions of the perfused organ. The effluent from the perfusion through the organ or tissue is collected in a venous return reservoir where the re-circulated solution is reheated, reoxygenated, nutrients replenished and the pH adjusted. After such treatment, the circulating solution is collected and stored in the arterial reservoir for recirculation.

Example 2

Seeding of Cells in the Organ

Human progenitor renal epithelial cells (REC) were isolated from the tubules within the cortex of human kidneys using methods known to those of skill in the art. Briefly, the cortex was excised from the kidney and the tissue was minced into approximately 2 mm pieces. The pieces were then enzymatically digested with collagenase and DNase in the presence of soybean trypsin inhibitor. The resulting slurry was passed through a sieve to collect particles of less than 212 µm size. The digestion and sieving was repeated to maximize yield. The cell suspension was then washed and plated into tissue culture flasks in a medium consisting of UltraMDCK, 1× insulin-transferrin-ethanolamine and selenium, 6 pM triodothyronine, 1× antibiotic, antimycotic, and 10 ng/ml of epidermal growth factor.

While the cells were in a non-confluent state, confirmation that renal progenitor cells were isolated was performed using phase-contrast and immunofluorescence microscopy. Under phase-contrast, the isolated progenitor cells are monomorphic with a spindle-shaped morphology and contain scant cytoplasm. Immunofluorescence microscopy was performed using anti-vimentin antibody and an anti-cytokeratin antibody; the progenitor renal cells were positive for vimentin and cytokeratin negative.

When the cultures reached a confluent state, retinoic acid 300 mg/L was added to the medium as a differentiation factor for tubule epithelium cells. Immunofluorescence detection of the antibodies anti-acetylated tubulin and anti-γ glutamyl-transpeptidase were used for markers to confirm that the isolated cells were tubular epithelial cells.

The REC were fluorescently labeled with PKH26 red fluorescent cell linker. Porcine kidneys were damaged by 60-minutes of postmortem warm ischemia. The damaged kidneys were then flushed and placed on the warm perfusion system with ex vivo acellular near-normothermic perfusion at 32° C. for 60 minutes to restore oxidative metabolism and normalize perfusion pressures and vascular flow rates. Fluorescently-labeled human REC ($50 \times 10^7$) were then infused into the renal artery at the rate of $-0.5 \times 10^6$ cells/minute. The perfusion was continued for an additional 8 hours.

Figure 2:
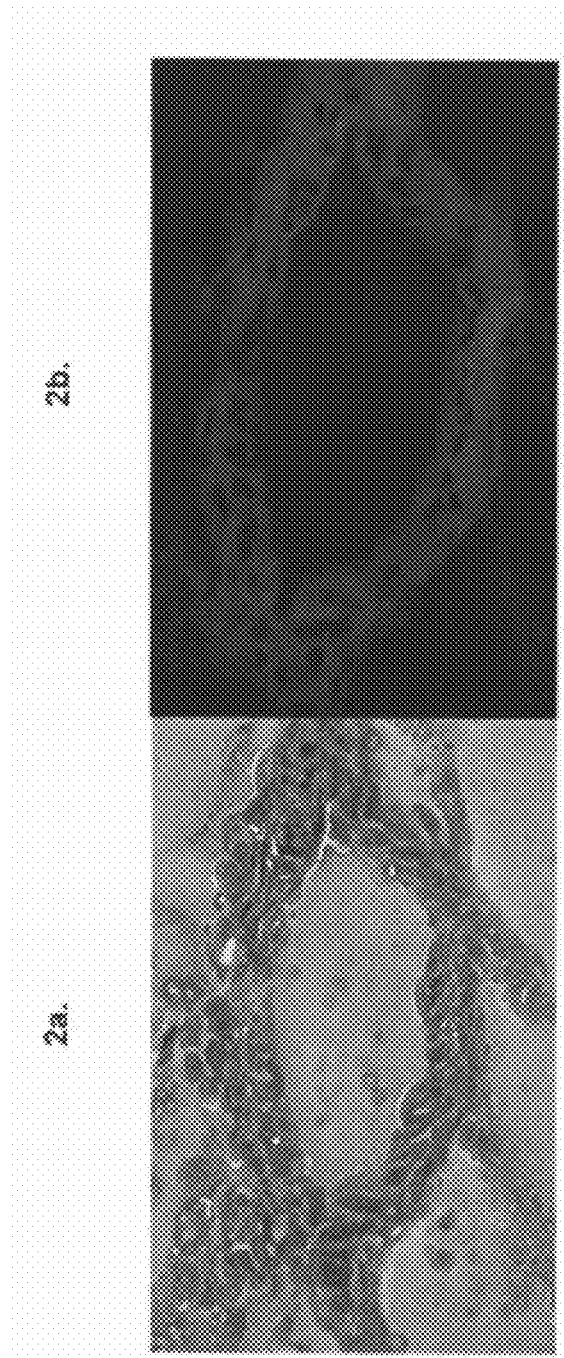
FIG. 2 are micrographs showing the results of using a warm perfusion system to deliver exogenous cells to a perfused kidney.

During the administration of the REC there were no adverse vascular reactions. The perfusion pressures, vascular flow rates and oxygen consumption of the kidney remained stable during the 8 hours of post-treatment perfusion. Post-perfusion, the labeled human REC were only detected within the renal tubule epithelium. More than 90% of the fluorescently labeled human REC were taken up by the kidney and could be detected predominantly in the tubules of the outer medulla. (FIGS. 2a and 2b)

Example 3

Tissue Engineering of the Vasculature of the Kidney

Human renal allografts (n=4) that were procured for (but later rejected) clinical transplantation were transitioned from hypothermic preservation to near-normothermic, acellular perfusion via the warm perfusion system. During three hours of ex vivo warm perfusion, extracellular basement proteins were administered through the sampling port in the arterial line and allowed to polymerize along the vasculature within human kidneys. Following polymerization, $1.0 \times 10^8$ vascular endothelial cells isolated from human umbilical cord veins (HUVEC) that had been labeled with a green fluorescent cell membrane linker were introduced into the recirculating pathway for delivery to the kidneys. Following 12 hours of continued perfusion, few HUVEC remained in the perfusion solution (less than $2.0 \times 10^6$).

Frozen sections from the kidneys were evaluated by fluorescent microscopy. The labeled HUVEC were found exclusively along the vascular lumen resulting in the formation of blood vessels with native basement membrane covered with native vascular endothelium sandwiched beneath the tissue engineered basement membrane covered by the labled seeded HUVEC (data not shown).

Although a presently contemplated best mode and alternative modes of practicing the invention has been disclosed by reference to the illustrative embodiments described above, it will be apparent to those skilled in the art from a consideration of the foregoing description that variations and modification s may be made without deparing from the spirit of the invention. Accordingly , it is intended that all such changes and modifications that fall within the true spirit and scope of the invention be encompassed by the appended claims.

The invention claimed is:

1. A method for the delivery of cell-based therapeutic agent to an ischemically damaged target tissue or organ, the method comprising:
(a) isolating the ischemically damaged target tissue or organ from the circulatory system of a body;
(b) flushing the ischemically damaged tissue or organ with a non-blood buffered physiological solution to remove blood and blood products;
(c) perfusing the tissue or organ in a recirculating warm perfusion solution capable of maintaining the tissue or organ at a near-normal metabolic rate;

(d) introducing cells and/or a cell-based therapeutic agent into the perfusion solution;

(e) perfusing the tissue or organ for a time sufficient for cells to become engrafted in the tissue or organ.

2. The method of claim 1, wherein the cells are exogenous cells.

3. The method of claim 1, wherein the cells are autologous cells.

4. The method of claim 1, wherein the cells are selected from the group consisting of embryonic stem cells, adult stem cells, and progenitor cells.

5. The method of claim 1, wherein said perfusion system has a closed perfusion pathway.

6. The method of claim 1, wherein said warm perfusion solution comprises at least one chemical energy substrate chosen from the group consisting of coenzyme A, FAD, DPN, Cocarboxylase, TPN, ATP, AMP, and UTP.

7. A method for the restoration of a damaged tissue or organ, the method comprising:

a. establishing the damaged tissue or organ in a perfusion system capable of maintaining the tissue or organ at a near-normal metabolic rate, the system comprising a warm perfusion solution;

b. introducing cells or a cell-based therapeutic agent into the perfusion solution;

c. perfusing the damaged tissue or organ for a time sufficient for cells to become engrafted in the tissue or organ.

8. A method for the delivery of cells and/or a cell-based therapeutic agent to a target tissue or organ, the method comprising:

(a) isolating said target tissue or organ from the circulatory system of a body;

(b) flushing the tissue or organ with a non-blood buffered physiological solution to remove blood and blood products from the tissue or organ;

(c) maintaining the target tissue or organ in a perfusion system with a recirculating non-blood perfusion solution at 25-37° C., to maintain the tissue or organ in a near normal metabolic state; and (d) contacting the tissue or organ with the cell/cell-based therapeutic agent by adding the cells/agent to the recirculating non-blood perfusion solution during perfusion.

9. The method of claim 8 further comprising returning the tissue or organ to the circulatory system of the body.

\* \* \* \* \*